US007933650B2

United States Patent
Li

(10) Patent No.: US 7,933,650 B2
(45) Date of Patent: Apr. 26, 2011

(54) METHOD AND APPARATUS FOR SELECTING AND TIMING ANTI-TACHYARRHYTHMIA PACING USING CARDIAC SIGNAL MORPHOLOGY

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1122 days.

(21) Appl. No.: 11/276,162

(22) Filed: Feb. 16, 2006

(65) Prior Publication Data

US 2007/0191894 A1   Aug. 16, 2007

(51) Int. Cl.
*A61N 1/362* (2006.01)
(52) U.S. Cl. ............................................. 607/14; 607/9
(58) Field of Classification Search .................. 600/510, 600/515–518; 607/4, 9, 14
See application file for complete search history.

(56) References Cited

U.S. PATENT DOCUMENTS

| 5,306,293 | A * | 4/1994 | Zacouto ........................... 607/17 |
| 6,539,254 | B1 * | 3/2003 | Kroll ................................. 607/4 |
| 6,775,572 | B2 | 8/2004 | Zhu et al. |
| 6,801,806 | B2 | 10/2004 | Sun et al. |
| 6,838,591 | B2 | 1/2005 | Waksmundzki et al. |
| 7,228,176 | B2 * | 6/2007 | Smith et al. ...................... 607/28 |
| 2002/0143264 | A1 * | 10/2002 | Ding et al. ..................... 600/510 |
| 2003/0023273 | A1 * | 1/2003 | DeGroot et al. ................... 607/4 |
| 2003/0139780 | A1 * | 7/2003 | Markowitz et al. .............. 607/17 |
| 2004/0088014 | A1 * | 5/2004 | Burnes ............................. 607/14 |
| 2004/0220624 | A1 | 11/2004 | Ritscher et al. |
| 2004/0220634 | A1 | 11/2004 | Belk |
| 2004/0236379 | A1 * | 11/2004 | Bardy et al. ....................... 607/9 |
| 2005/0090869 | A1 | 4/2005 | Sun et al. |
| 2007/0142866 | A1 | 6/2007 | Li |
| 2007/0173894 | A1 | 7/2007 | Li |

* cited by examiner

*Primary Examiner* — Carl H Layno
*Assistant Examiner* — Jennifer Stewart
(74) *Attorney, Agent, or Firm* — Schwegman, Lundberg & Woessner, P.A.

(57) ABSTRACT

A cardiac rhythm management (CRM) system includes an implantable medical device that delivers anti-tachyarrhythmia therapies including ATP. When a tachyarrhythmia episode is detected, the implantable medical device analyzes the morphology of a cardiac signal to determine whether and/or when to deliver an ATP therapy. In various embodiments, the implantable medical device produces morphological parameters indicative of the likeliness of success of the ATP therapy and selects an anti-tachyarrhythmia therapy mode based on the morphological parameters. In various embodiments, the implantable medical device also controls the timing of the ATP therapy delivery using morphological features of the cardiac signal to maximize the probability that the ATP therapy is delivered into an ATP window during which a tachyarrhythmia episode can be effectively terminated by pacing.

19 Claims, 10 Drawing Sheets

METHOD AND APPARATUS FOR SELECTING AND TIMING ANTI-TACHYARRHYTHMIA PACING USING CARDIAC SIGNAL MORPHOLOGY

TECHNICAL FIELD

This document relates generally to cardiac rhythm management (CRM) systems and particularly, but not by way of limitation, to a system that controls the selection and timing of anti-tachyarrhythmia pacing (ATP) therapy based on cardiac signal morphology.

BACKGROUND

Tachyarrhythmias are abnormal heart rhythms characterized by a rapid heart rate. Tachyarrhythmias generally include supraventricular tachyarrhythmia (SVT, including atrial tachyarrhythmia, AT) and ventricular tachyarrhythmia (VT). Fibrillation is a form of tachyarrhythmia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrioventricular sequence and synchrony to result in efficient blood-pumping functions indicated by a normal hemodynamic performance. VT occurs when the electrical impulses propagate along a pathologically formed self-sustaining conductive loop within the ventricles or when a natural pacemaker in a ventricle usurps control of the heart rate from the sinoatrial node. When the atria and the ventricles become dissociated during VT, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a cardiac rhythm management (CRM) device that delivers an electric shock to terminate a detected tachyarrhythmia episode by depolarizing the entire myocardium simultaneously and rendering it refractory.

Another type of electrical therapy for tachyarrhythmia is anti-tachyarrhythmia pacing (ATP). In ATP, the heart is competitively paced in an effort to interrupt the reentrant loop causing the tachyarrhythmia. An exemplary ICD includes ATP and defibrillation capabilities so that ATP is delivered to the heart when a non-fibrillation VT is detected, while a defibrillation shock is delivered when fibrillation occurs. Although cardioversion and/or defibrillation are effective in terminating tachyarrhythmia, it consumes a large amount of power and results in patient discomfort owing to the high voltage of the shock pulses. It is desirable, therefore, for the ICD to use ATP to terminate a tachyarrhythmia whenever possible.

The efficacy of ATP in terminating tachyarrhythmia depends on the type of the tachyarrhythmia and the timing of ATP delivery. To be effective, an ATP therapy is to be delivered to the heart during an excitable gap in the reentrant loop. Inaccurate timing of an ATP delivery is known to contribute to the failure in terminating tachyarrhythmia using ATP.

For these and other reasons, there is a need for determining whether and when to deliver an ATP therapy.

SUMMARY

A CRM system includes an implantable medical device that delivers anti-tachyarrhythmia therapies including ATP. When a tachyarrhythmia episode is detected, the implantable medical device analyzes the morphology of a cardiac signal to determine whether and/or when to deliver an ATP.

In one embodiment, a CRM system includes a sensing circuit, a tachyarrhythmia detection and classification module, a pacing output circuit, and an ATP controller. The sensing circuit senses one or more cardiac signals. The tachyarrhythmia detection and classification module detects and classifies a tachyarrhythmia episode using the one or more cardiac signals. The pacing output circuit delivers pacing pulses. The ATP controller initiates and times an ATP therapy using the classification of the detected tachyarrhythmia episode and morphology of one of the one or more cardiac signals. The ATP controller includes an ATP selection module and an ATP timing module. The ATP selection module includes a morphological parameter generator and an ATP selector. The morphological parameter generator produces one or more morphological parameters using the one or more cardiac signals. The one or more morphological parameters are indicative of a likeliness of success of the ATP therapy. The ATP selector selects a therapy mode using the one or more morphological parameters. The ATP timing module produces and times an ATP interval using the morphology of the one of the one or more cardiac signals and to initiate the delivery of the ATP therapy when the ATP interval expires.

In one embodiment, a CRM system includes a sensing circuit, a cycle length detector, a tachyarrhythmia detector, a tachyarrhythmia classifier, a pacing output circuit, and an ATP selection module. The sensing circuit senses one or more cardiac signals. The cycle length detector detects cardiac cycle lengths from the one or more cardiac signals. The cardiac cycle lengths are each a time interval between two consecutively detected heart beats. The tachyarrhythmia detector detects a tachyarrhythmia episode using the cardiac cycle lengths. The tachyarrhythmia classifier classifies the detected tachyarrhythmia episode. The pacing output circuit delivers pacing pulses. The ATP selection module selects a therapy mode based on the classification of the detected tachyarrhythmia episode and morphology of one of the one or more cardiac signals. The ATP selection module includes a morphological parameter generator and an ATP selector. The morphological parameter generator detects QRS widths from the one of the one or more cardiac signals and calculates one or more morphological parameters using the QRS widths and the cardiac cycle lengths. The ATP selector selects the therapy mode using the one or more morphological parameters.

In one embodiment, a CRM system includes a sensing circuit, a tachyarrhythmia detection and classification module, a pacing output circuit, and an ATP timing module. The sensing circuit senses one or more cardiac signals. The tachyarrhythmia detection and classification module detects and classifies a tachyarrhythmia episode using the one or more cardiac signals. The pacing output circuit delivers pacing pulses. The ATP timing module times the delivery of the pacing pulses according to an ATP mode using morphology of one of the one or more cardiac signals. The ATP timing module includes an ATP timer, a morphology-based reference point detector, and a morphology-based ATP interval generator. The ATP timer starts timing an ATP interval from an ATP reference point. The morphology-based reference point detector detects the ATP reference point. The ATP reference point is a predetermined type fiducial point on the one of one or more cardiac signals. The morphology-based ATP interval generator produces the ATP interval using the morphology of the one of the one or more cardiac signals.

In one embodiment, a method for controlling ATP is provided. One or more cardiac signals are sensed. A tachyarrhythmia episode is detected and classified using the one or more cardiac signals. One or more morphological parameters are derived using the one or more cardiac signals. The one or more morphological parameters are indicative of a likeliness of success of an ATP therapy. Whether to deliver the ATP therapy is determined based on the one or more morphological parameters.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
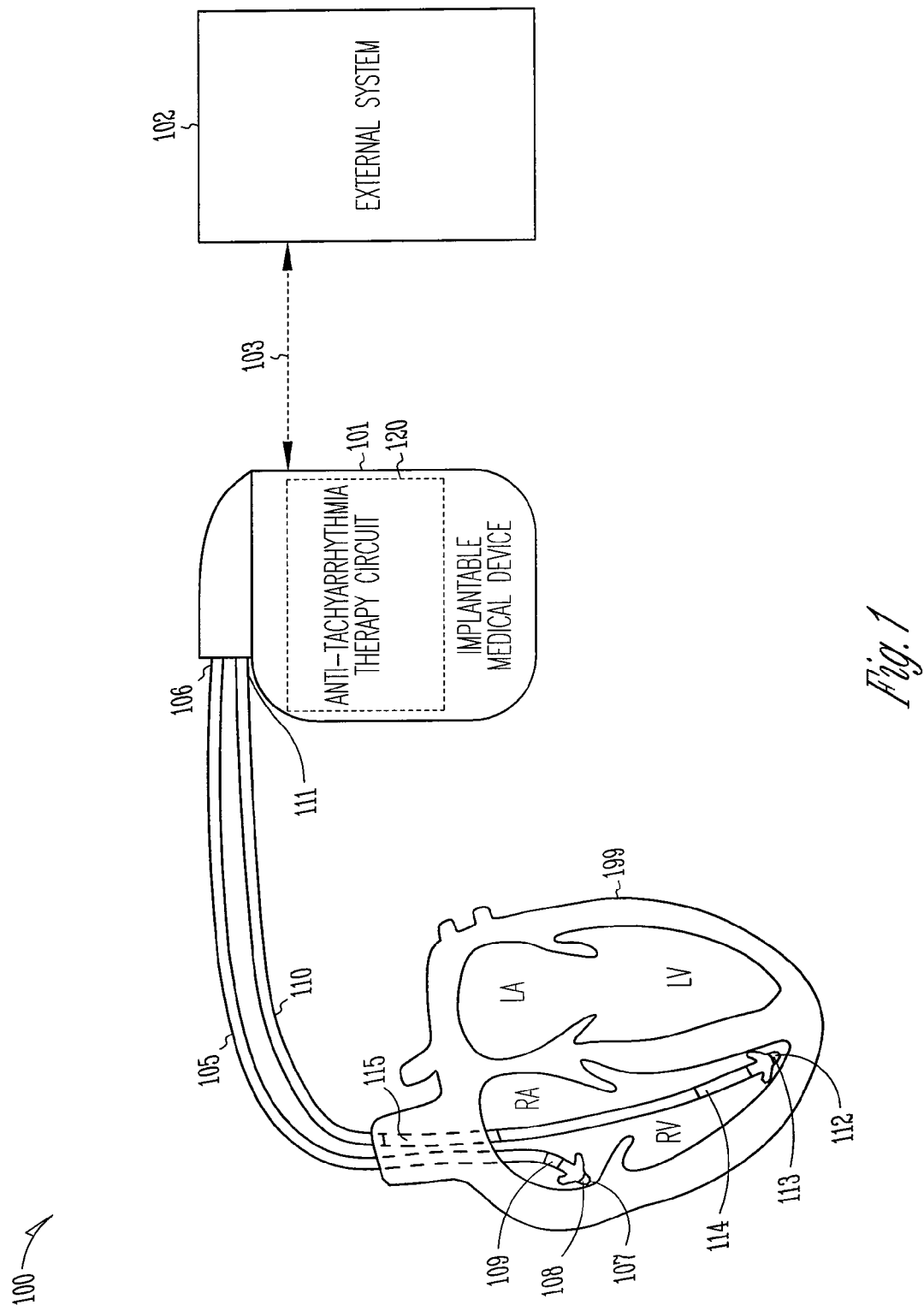
FIG. 1 is an illustration of an embodiment of a CRM system including an implantable medical device that selects and times anti-tachyarrhythmia therapies using cardiac signal morphology and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

In this document, "mean" (such as in a "mean feature correlation coefficient") includes mean and other notations of central tendency, such as average and median.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

This document discusses a CRM system that delivers anti-tachyarrhythmia therapies including ATP and controls the anti-tachyarrhythmia therapies, including selection and timing of the ATP, based on cardiac signal morphology. An ATP therapy is most effective when delivered within an "excitable gap" after ventricular repolarization (T wave) and before ventricular depolarization (R wave). The delivery of an ATP therapy is typically initiated at the end of a "coupled interval" (CI), which starts with a ventricular depolarization and has a length intended to end during the excitable gap. The coupling interval is typically calculated as a percentage of a cardiac cycle length. The cardiac cycle length may be an average cardiac cycle length being the average of time intervals between two consecutive ventricular depolarizations. The ATP therapy is most effective when the excitable gap is wide and the cardiac cycle length is substantially stable (with small variations). When the excitable gap is narrow and/or when the cardiac cycle length is substantially unstable, the ATP is more likely delivered outside the excitable gap and therefore ineffective in terminating a tachyarrhythmia episode. The present CRM system determines whether to select an ATP therapy for terminating a tachyarrhythmia episode by analyzing morphological characteristics of a cardiac signal that indicate the width of the excitable gap and the stability of that width over a period of time. The ATP therapy is selected when the morphological characteristics of the cardiac signal indicate a reasonably wide excitable gap. If the ATP therapy is selected when the width of the excitable gap is reasonably wide but not substantially stable, the timing of ATP delivery is determined using detectable morphological features of the cardiac signal.

FIG. 1 is an illustration of an embodiment of a CRM system 100 and portions of the environment in which CRM system 100 operates. CRM system 100 includes an implantable medical device 101 that is electrically coupled to a heart 199 through one or more electrodes, such as on leads 105 and 110. An external system 102 communicates with implantable medical device 101 via a telemetry link 103.

Implantable medical device 101 delivers anti-tachyarrhythmia therapies including ATP and cardioversion/defibrillation therapies. In one embodiment, implantable medical device 101 is an implantable cardioverter/defibrillator (ICD) with cardiac pacing capabilities. In another embodiment, in addition to a pacemaker and a cardioverter/defibrillator, implantable medical device 101 further includes one or more of other monitoring and/or therapeutic devices such as a neural stimulator, a drug delivery device, and a biological therapy device. Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is typically a pacing lead that includes a proximal end 106 connected to implantable medical device 101 and a distal end 107 placed in the right atrium (RA) of heart 199. A pacing-sensing electrode 108 (referred to as the "RA tip" electrode) is located at distal end 107. Another pacing-sensing electrode 109 (referred to as the "RA ring" electrode) is located near distal end 107. Electrodes 108 and 109 are electronically connected to implantable medical device 101 via separate conductors in lead 105 to allow sensing of the atrial electrogram and/or delivery of atrial pacing pulses. Lead 110 is typically a defibrillation lead that includes a proximal end 111 connected to implantable medical device 101 and a distal end 112 placed in the right ventricle (RV) of heart 199. A pacing-sensing electrode 113 (referred to as the "RV tip" electrode) is located at distal end 112. A defibrillation electrode 114 (referred to as the "RV coil" electrode) is located near distal end 112 but electrically separated from pacing-sensing electrode 113. Another defibrillation electrode 115 (referred to as the "SVC coil" electrode) is located at a distance from distal end 112 for placement in the superior vena cava (SVC). In one embodiment, electrode 115 is electrically connected to the hermetically sealed can. Electrodes 113, 114, and 115 are electrically connected to implantable medical device 101 via separate conductors in lead 110. Electrode 113 allows sensing of the ventricular electrogram and/or delivery of ventricular pacing pulses. Electrodes 114 and 115 allow sensing of the ventricular electrogram and/or delivery of ventricular cardioversion/defibrillation pulses.

Implantable medical device 101 includes an anti-tachyarrhythmia therapy circuit 120 that selects and times anti-tachyarrhythmia therapies using cardiac signal morphology indicative of the likeliness of success of an ATP therapy. In various embodiments, anti-tachyarrhythmia therapy circuit 120 provides implantable medical device 101 with ATP and cardioversion/defibrillation therapy modes. An ATP therapy mode is selected when the cardiac signal morphology indicates a reasonably wide excitable gap. When the cardiac signal morphology indicates that the width of the excitable gap is reasonably wide but not substantially stable, cardiac signal morphology is also analyzed to determine the timing of delivery for the selected ATP therapy. Various embodiments of system 120 are discussed below, with reference to FIGS. 3-8. In various embodiments, implantable medical device 101 also includes one or more of other cardiac electrical therapy circuits such as an anti-bradyarrhythmia circuit, a cardiac resynchronization therapy (CRT) circuit, a cardiac remodeling control therapy (RCT) circuit.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status and adjusting therapies. Telemetry link 103 is a wireless communication link providing for bidirectional data transmission between implantable medical device 101 and external system 102. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), programming implantable medical device 101 to enable an available monitoring or therapeutic function (such as ATP), and programming implantable medical device 101 to adjust therapeutic parameters such as pacing and/or cardioversion/defibrillation parameters.

Figure 2:
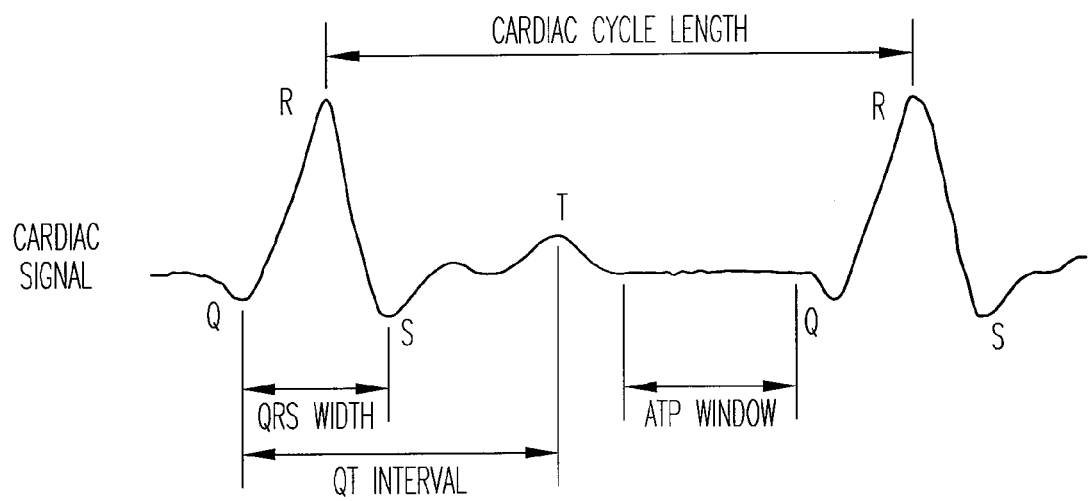
FIG. 2 is an illustration showing an ATP window indicated on a sensed cardiac signal.

FIG. 2 is an illustration showing an ATP window indicated on a sensed cardiac signal. The cardiac signal, such as a ventricular electrogram sensed through the RV coil and SVC coil electrodes, is indicative of QRS complexes and T waves. For effectiveness, an ATP therapy is to be delivered during the ATP window, which corresponds to the excitable gap and starts after the T wave and ends before the QRS complex. For a given cardiac cycle length, a lengthened QT interval (time interval between the Q wave and the T wave) shortens the ATP window. Thus, the ratio of QT interval to the cardiac cycle length provides for an indication of probability of a successful delivery of the ATP therapy, with a smaller ratio indicating a higher probability of success. However, QT interval may be difficult to detect by an implantable medical device during tachyarrhythmia because the T wave may not appear when the heart rate is fast, or because the T wave is filtered out by the sensing circuit. An alternative is to use the ratio of QRS width (duration of the QRS complex) to the cardiac cycle length as the indication of probability of a successful delivery of the ATP therapy, again with a smaller ratio indicating a higher probability of success. Therefore, the morphological characteristics of the sensed cardiac signal, including the QT interval or the QRS width measured relative to the cardiac cycle length, provides for a basis for selecting an anti-tachyarrhythmia therapy in system 100.

Figure 3:
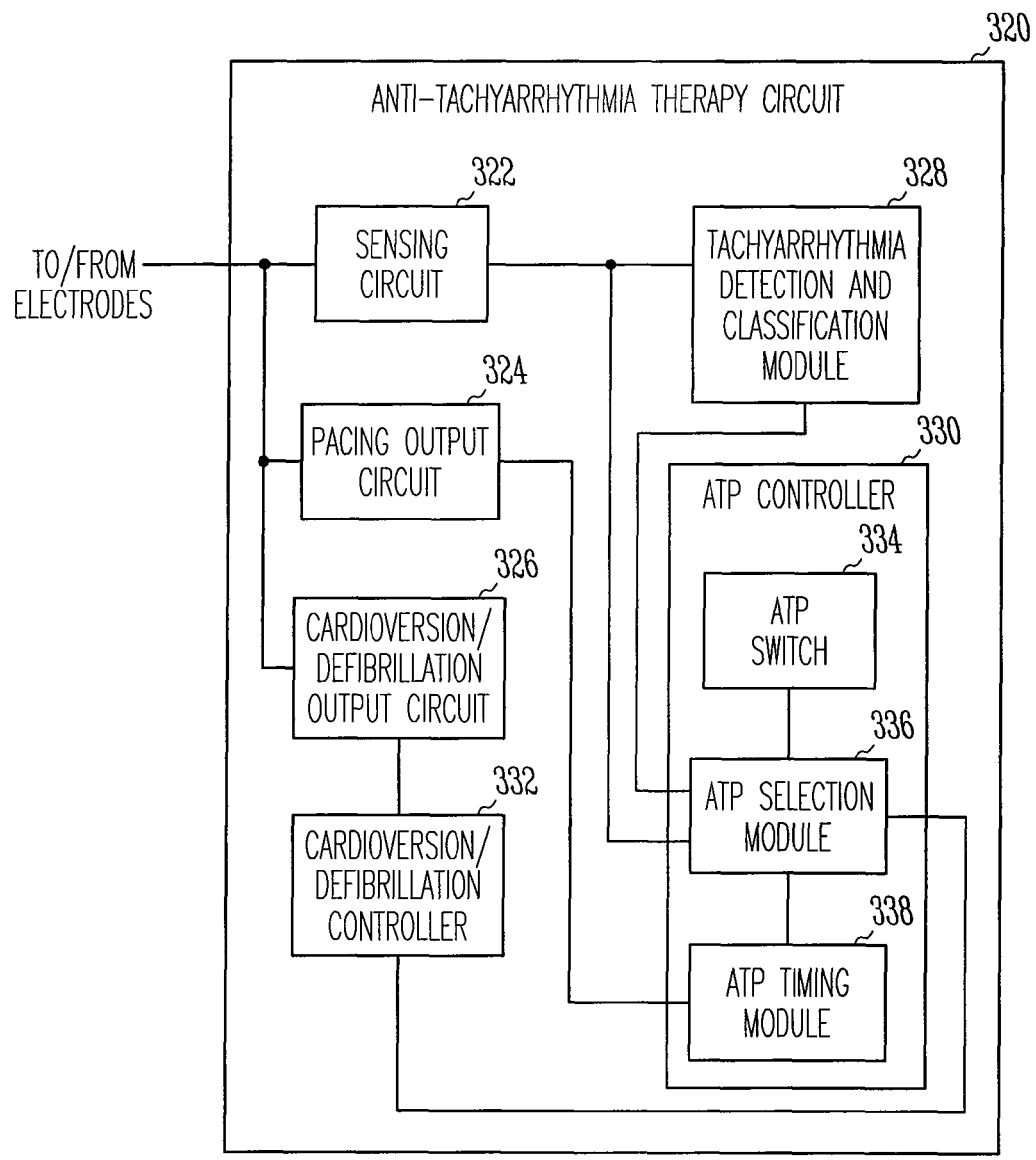
FIG. 3 is a block diagram illustrating an embodiment of an anti-tachyarrhythmia therapy circuit of the implantable medical device.

FIG. 3 is a block diagram illustrating an embodiment of an anti-tachyarrhythmia therapy circuit 320, which is a specific embodiment of anti-tachyarrhythmia therapy circuit 120. Anti-tachyarrhythmia therapy circuit 320 includes a sensing circuit 322, a pacing output circuit 324, a cardioversion/defibrillation output circuit 326, a tachyarrhythmia detection and classification module 328, an ATP controller 330, and a cardioversion/defibrillation controller 332.

Sensing circuit 322 senses one or more cardiac signals from heart 199 through electrodes such as those selected from electrodes 108, 109, 113, 114, 115, and the hermetically sealed can of implantable medical device 101. Pacing output circuit 324 delivers pacing pulses to heart 199 through electrodes such as those selected from electrodes 108, 109, 113, and the hermetically sealed can. Cardioversion/defibrillation output circuit 326 delivers cardioversion/defibrillation pulses to heart 199 through electrodes such as those selected from electrodes 114, 115, and the hermetically sealed can. Tachyarrhythmia detection and classification module 328 detects and classifies tachyarrhythmia episodes using the one or more cardiac signals. ATP controller 330 controls the delivery of the pacing pulses according to an ATP mode based on the classification of each detected tachyarrhythmia episode and the morphology of the one or more cardiac signals. Cardioversion/defibrillation controller 332 controls the delivery of the cardioversion/defibrillation pulses based on the classification of the detected tachyarrhythmia episode, whether the ATP mode is selected, and the result of the ATP therapy if the ATP mode is selected.

ATP controller 330 includes an ATP switch 334, an ATP selection module 336, and an ATP timing module 338. ATP switch 334 allows for the activation and deactivation of ATP therapy by programming, such as by a user through external system 102. ATP controller 330 controls the delivery of the pacing pulses according to an ATP mode when the ATP therapy is activated. ATP selection module 336 derives one or more morphological parameters from the one or more cardiac signals and selects a therapy mode using the one or more morphological parameters. The one or more morphological parameters are indicative of the likeliness of success of the ATP therapy. ATP timing module 338 produces and times an ATP interval using the morphology of the one or more cardiac signals and initiates the delivery of the ATP therapy when the ATP interval expires. In one embodiment, each delivery of the ATP therapy includes the delivery of at least one burst of pacing pulses. The burst of pacing pulses includes approximately 3 to 10 pacing pulses, with approximately 5 pacing pulses as a specific example, delivered at a pacing rate of approximately 200 to 250 pulses per minute, with approximately 200 pulses per minute as a specific example.

In one embodiment, ATP controller 330 also controls the delivery of the pacing pulse according to an ATP-BC (ATP before charge) mode. The ATP-BC mode provides for an attempt to terminate the detected tachyarrhythmia episode using ATP immediately before charging a defibrillation capacitor of cardioversion/defibrillation output circuit 326. The defibrillation capacitor stores energy for a cardioversion/defibrillation pulse and is charged for the delivery of each cardioversion/defibrillation pulse. An example of ATP-BC is discussed in U.S. patent application Ser. No. 10/817,751, entitled "METHOD AND APPARATUS FOR ANTI-TACHYARRHYTHMIA PACING AND DEFIBRILLATION," filed on Apr. 2, 2004, assigned to Cardiac Pacemakers, Inc., which is incorporated herein by reference in its entirety. In one embodiment, if the ATP mode is not selected by ATP selection module 336, the ATP-BC mode is selected as the next more aggressive therapy. In another embodiment, if the ATP mode is not selected by ATP selection module 336, a cardioversion/defibrillation mode is selected as the next more aggressive therapy.

In various embodiments, implantable medical device 101 is a pacemaker-defibrillator that provides one or more pacing therapies in addition to the anti-tachyarrhythmia therapies. In addition to anti-tachyarrhythmia therapy circuit 320, implantable medical device 101 includes a pacing controller that controls the delivery of the pacing pulses from pacing output circuit 324 according to a bradycardia pacing mode, a cardiac resynchronization therapy (CRT) mode, or a cardiac remodeling control therapy (RCT) mode.

Figure 4:
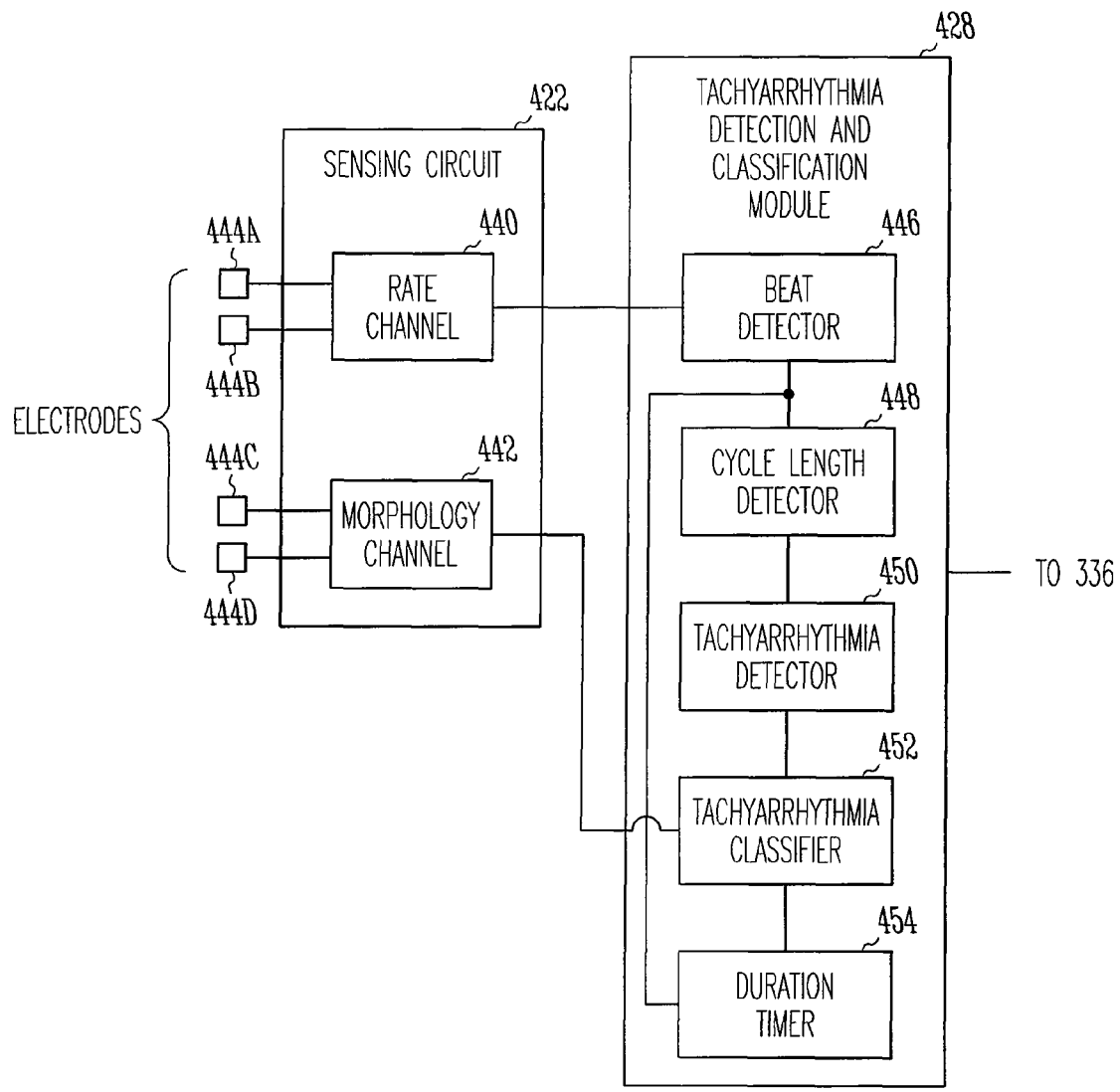
FIG. 4 is a block diagram illustrating an embodiment of a sensing circuit and a tachyarrhythmia detection and classification module of the anti-tachyarrhythmia therapy circuit.

FIG. 4 is a block diagram illustrating an embodiment of a sensing circuit 422 and a tachyarrhythmia detection and classification module 428. Sensing circuit 422 is a specific embodiment of sensing circuit 322 and senses cardiac signals through an electrode system including electrodes 444A-D. Tachyarrhythmia detection and classification module 428 is a specific embodiment of tachyarrhythmia detection and classification module 328.

Sensing circuit 422 includes a rate channel 440 and a morphology channel 442.

Rate channel 440 senses a regional cardiac signal through electrodes 440A and 440B for use in heart beat detection. Morphology channel 442 senses a global cardiac signal through electrodes 440C and 440D for use in morphological analysis.

In one embodiment, rate channel 440 senses a regional ventricular electrogram through an RV tip electrode such as electrode 113 and an RV coil electrode such as electrode 114, and morphology channel 442 senses a global ventricular electrogram through the RV coil electrode and an SVC coil electrode such as electrode 115. In this embodiment, electrode 444A is the RV tip electrode, electrodes 444B and 444C are the same RV coil electrode, and electrode 444D is the SVC coil electrode. In one embodiment, the SVC coil electrode is electrically connected to the hermetically sealed can of implantable medical device 101. Because cardioversion/defibrillation pulses (shocks) are also delivered using the RV coil electrode and the SVC coil electrode, morphology channel 442 is also referred to as the shock channel. In an alternative embodiment, a single cardiac signal is sensed for use in heart rate detection and morphology analysis, such as through electrodes 440C and 440D. While this alternative embodiment eliminates the need for sensing two cardiac signals, the embodiment illustrated in FIG. 4 provides for an easier heart beat detection.

Tachyarrhythmia detection and classification module 428 include a beat detector 446, a cycle length detector 448, a tachyarrhythmia detector 450, a tachyarrhythmia classifier 452, and a duration timer 454. Beat detector 446 detects heart beats from the regional cardiac signal. In various embodiments, beat detector 446 detects cardiac depolarizations as the heart beats. Cycle length detector 448 detects cardiac cycle lengths each being a time interval between two consecutively detected heart beats. Tachyarrhythmia detector 450 detects the tachyarrhythmia episode using the cardiac cycle lengths. In one embodiment, tachyarrhythmia detector 450 detects the tachyarrhythmia episode by comparing the cardiac cycle lengths to one or more tachyarrhythmia detection thresholds. Tachyarrhythmia classifier 452 classifies the detected tachyarrhythmia episode using the global cardiac signal. In one embodiment, tachyarrhythmia classifier 452 classifies the detected tachyarrhythmia episode as one of VT and SVT. Duration timer 454 initiates a detection duration when the tachyarrhythmia episode is detected by tachyarrhythmia detector 450. In one embodiment, the detection duration is a pre-programmed constant duration in a range of approximately 1 to 30 seconds, with approximately 2.5 seconds as a specific example. Tachyarrhythmia classifier 452 classifies the detected tachyarrhythmia episode when the detection duration expires.

In the embodiment in which the regional cardiac signal is the regional ventricular electrogram and the global cardiac signal is the global ventricular electrogram, beat detector 446 detects ventricular depolarizations (R waves) as the hear beats from the regional ventricular electrogram. Cycle length detector 448 detects ventricular cycle lengths (also referred to as ventricular intervals or R-R intervals) each being a time interval between two consecutively detected ventricular depolarizations. Tachyarrhythmia detector 450 declares a detection of a VT episode when the ventricular cycle length falls within a VT detection zone for a predetermined number or percentage of heart beats. Tachyarrhythmia classifier 452 confirms the detection of the VT episode following the end of the detection duration by analyzing a morphology of the global ventricular electrogram.

Figure 5:
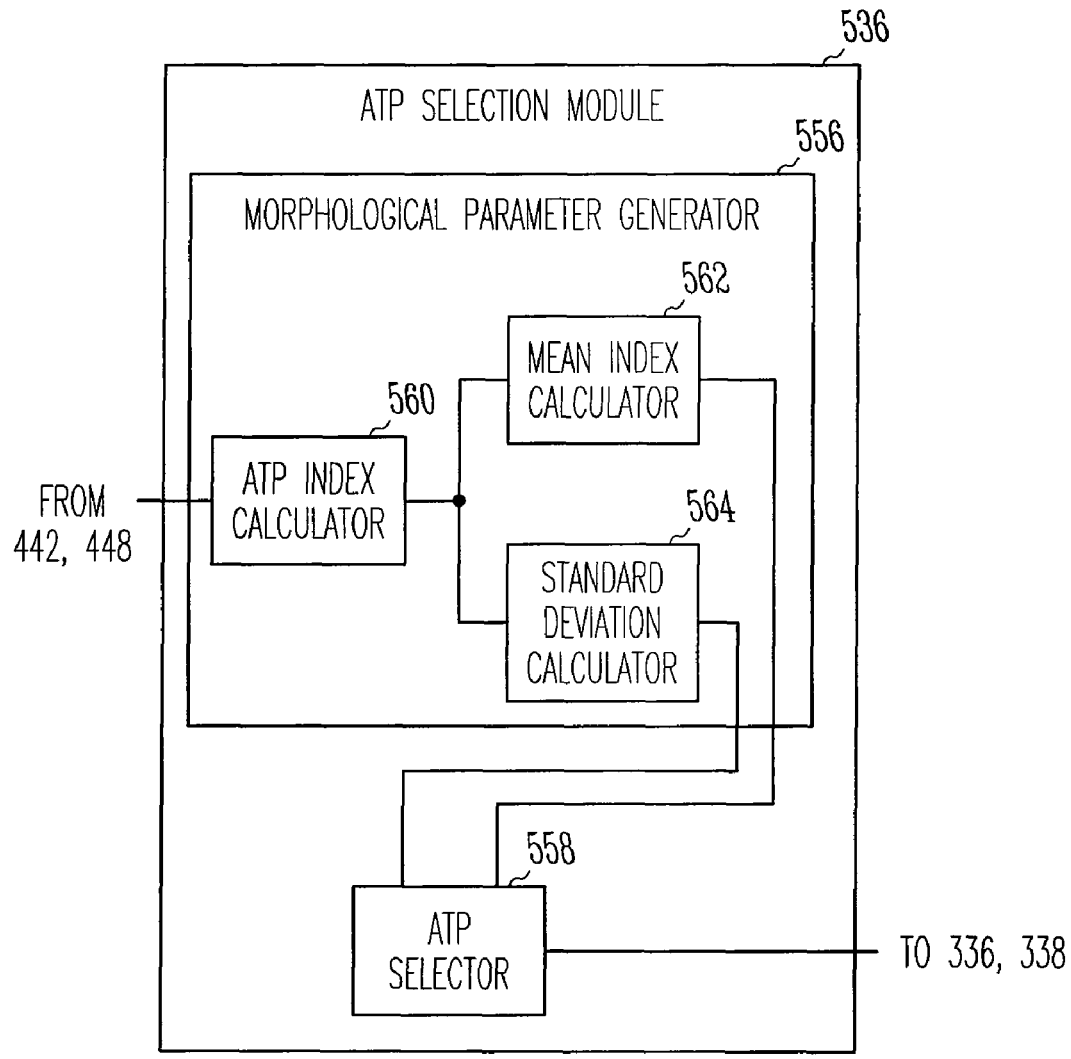
FIG. 5 is a block diagram illustrating an embodiment of an ATP selection module of the anti-tachyarrhythmia therapy circuit.

FIG. 5 is a block diagram illustrating an embodiment of an ATP selection module 536, which is a specific embodiment of ATP selection module 336. ATP selection module 536 includes a morphological parameter generator 556 and an ATP selector 558.

Figure 6:
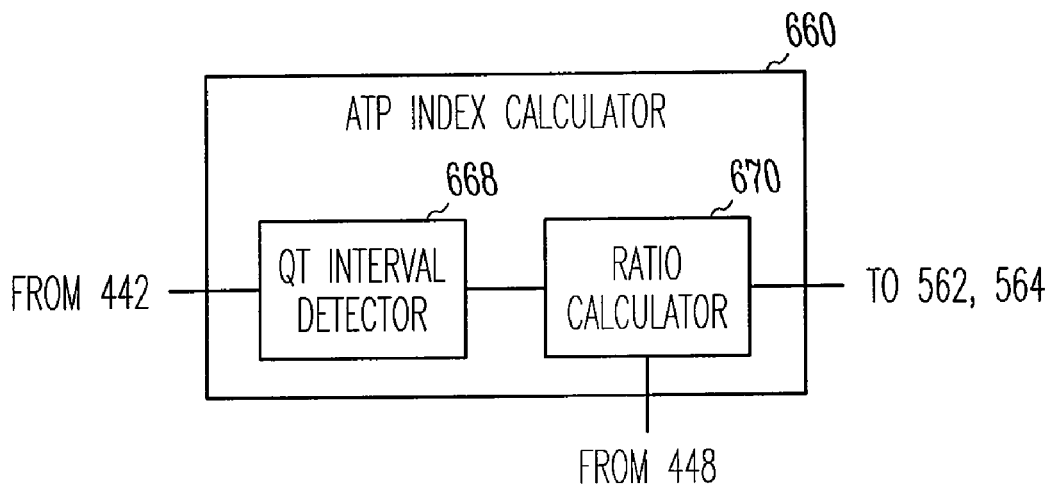
FIG. 6 is a block diagram illustrating an embodiment of an ATP index calculator of the ATP selection module.
Figure 7:
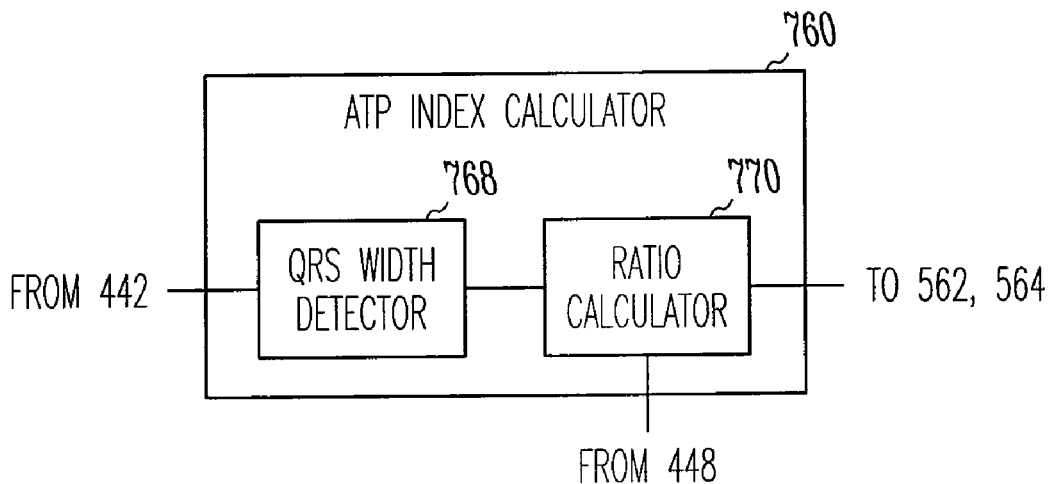
FIG. 7 is a block diagram illustrating another embodiment of the ATP index calculator.

Morphological parameter generator 556 includes an ATP index calculator 560, a mean index calculator 562, and a standard deviation calculator 564. ATP index calculator 560 calculates an ATP index for a heart beat. The ATP index is indicative of morphological characteristics of one or more cardiac signals during the heart beat. FIGS. 6 and 7 illustrate two specific embodiments of ATP index calculator 560. In FIG. 6, an ATP index calculator 660, which is a specific embodiment of ATP index calculator 560, includes a QT interval detector 668 and a ratio calculator 670. QT interval detector 668 detects the QT interval of the heart beat. Ratio calculator 670 calculates the ATP index as a ratio of the QT interval to the cardiac cycle length associated with the heart beat. In FIG. 7, an ATP index calculator 760, which is a specific embodiment of ATP index calculator 560, includes a QRS width detector 768 and a ratio calculator 770. QRS width detector 768 detects the QRS interval of the heart beat. Ratio calculator 770 calculates the ATP index as a ratio of the QRS width to the cardiac cycle length associated with the heart beat. While the ratio of the QT interval to the cardiac cycle length provides for a theoretically more accurate measure of the likeliness for a successful ATP therapy, the ratio of the QRS width to the cardiac cycle length may be more feasible to implement because of the difficulty of reliably detecting the T waves during tachyarrhythmia. Mean index calculator 562 calculates a mean ATP index of the ATP indexes calculated for heart beats detected during the detection duration. Standard deviation calculator 564 calculates a standard deviation of the ATP indexes calculated for the heart beats detected during the detection duration.

ATP selector 558 selects a therapy mode using the mean ATP index and the standard deviation. When the standard deviation is below a threshold standard deviation, and the mean index is below a threshold index, ATP selector 558 selects the ATP therapy with a default ATP mode using default ATP parameters. The default ATP parameters include one or more predetermined parameters and/or one or more parameters each being a predetermined function of a detected parameter such as the cardiac cycle length. When the standard deviation is below the threshold standard deviation and the mean index is above the threshold index, ATP selector 558 diverts from the ATP therapy to select a more aggressive therapy such as the cardioversion/defibrillation therapy or the ATP therapy according to the ATP-BC mode discussed above. When the standard deviation is above the threshold standard deviation and at least a predetermined number of ATP indexes are above the threshold index, ATP selector 558 also diverts from the ATP therapy to select the more aggressive therapy. When the standard deviation is above the threshold standard deviation and at least a predetermined number of ATP indexes are below the threshold index, ATP selector 558 selects the ATP therapy with a custom ATP mode. The custom ATP mode uses at least one ATP parameter being a function of the morphology of the one or more cardiac signals. In one embodiment, when the standard deviation is above the threshold standard deviation and at least a predetermined number of ATP indexes calculated for the last heart beats of the detection duration are below the threshold index, ATP selector 558 selects the ATP therapy with the custom ATP mode.

Figure 8:
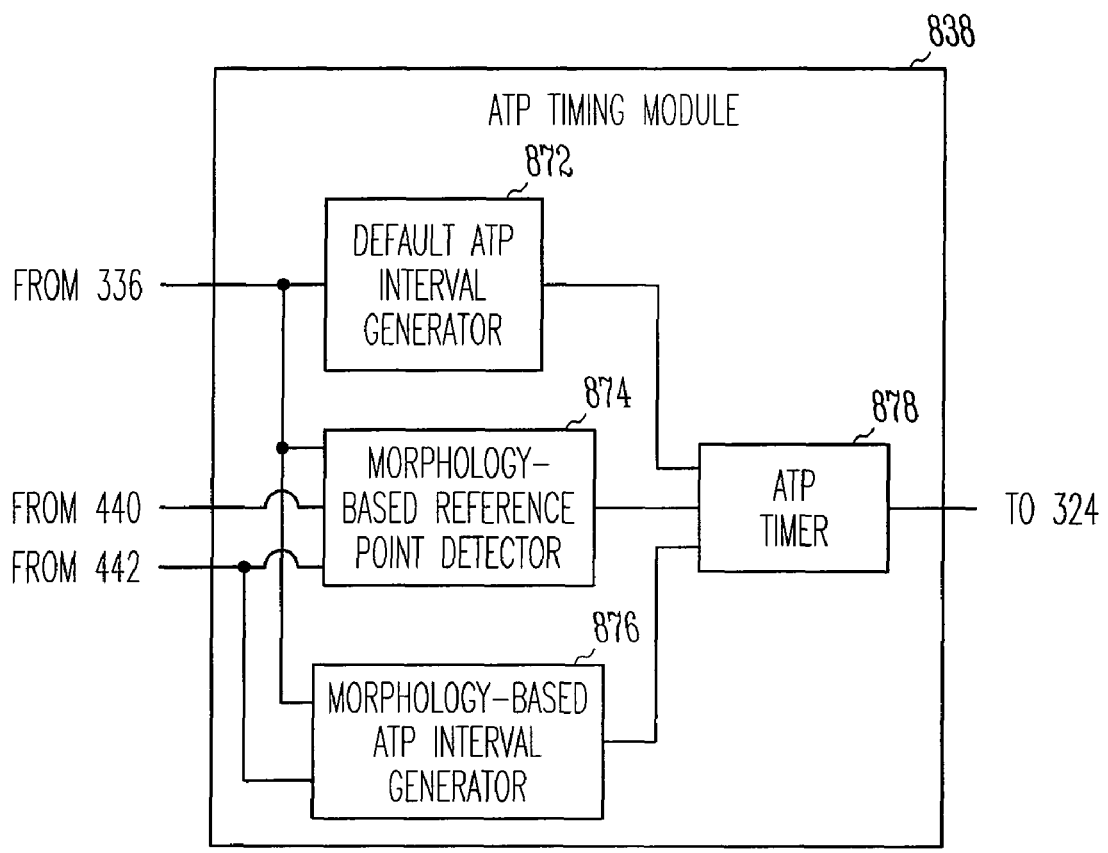
FIG. 8 is a block diagram illustrating an embodiment of an ATP timing module of the anti-tachyarrhythmia therapy circuit.

FIG. 8 is a block diagram illustrating an embodiment of an ATP timing module 838, which is a specific embodiment of ATP timing module 338. ATP timing module 838 includes a default ATP interval generator 872, a morphology-based reference point detector 874, a morphology-based ATP interval generator 876, and an ATP timer 878.

When the ATP therapy is selected by ATP selector 558, ATP timer 878 times an ATP interval from an ATP reference point and initiates the delivery of the ATP therapy when the ATP interval expires. The location of the ATP reference point and the length of the ATP interval depend on the mode of the ATP therapy selected.

Default ATP interval generator 872 produces a default ATP interval for use with the default ATP mode. In one embodiment, the default ATP interval starts from a ventricular depolarization and has a length being a percentage of the cardiac cycle length such as an average cardiac cycle length calculated for a plurality of consecutive heart beats that precede the ventricular depolarization from which the default ATP interval starts. This default ATP interval is known as the coupling interval. When ATP selector 558 selects the ATP therapy with the default ATP mode, ATP timer 878 times the default ATP interval produced by default ATP interval generator 872 and initiates the delivery of the ATP therapy when the default ATP interval expires.

Morphology-based reference point detector 874 detects a predetermined type fiducial point on the global cardiac signal to use as the ATP reference point. In one embodiment, morphology-based reference point detector 874 detects a regional peak in the regional cardiac signal during a cardiac cycle, a corresponding global peak in the global cardiac signal during the cardiac cycle, and a global trough adjacently following the global peak during the cardiac cycle. The ATP reference point is detected as the global trough if the global peak is between the regional peak and the global trough, or is the global peak if the global trough is between the regional peak and the global peak. This detection of the ATP reference point is further discussed below with reference to FIGS. 9 and 10. Morphology-based ATP interval generator 876 produces a custom ATP interval using the morphology of the global cardiac signal for use with the custom ATP mode. In one embodiment, morphology-based ATP interval generator 876 calculates the custom ATP interval as a product of a constant and the time interval between the global peak and the global trough. In a further embodiment, morphology-based ATP interval generator 876 adjusts the constant based on the effect of delivered ATP therapies. For example, the value of the constant is adjusted if the ATP therapy fails to terminate the detected tachyarrhythmia episode for a predetermined number of times. The value of the constant or the custom ATP interval associated with a substantially high rate of success in terminating tachyarrhythmia episodes using ATP is saved for use with future ATP therapies. When ATP selector 558 selects the ATP therapy with the custom ATP mode, ATP timer 878 times the custom ATP interval produced by morphology-based ATP interval generator 876 from the ATP reference point detected by morphology-based reference point detector 874 and initiates the delivery of the ATP therapy when the default ATP interval expires.

Figure 9:
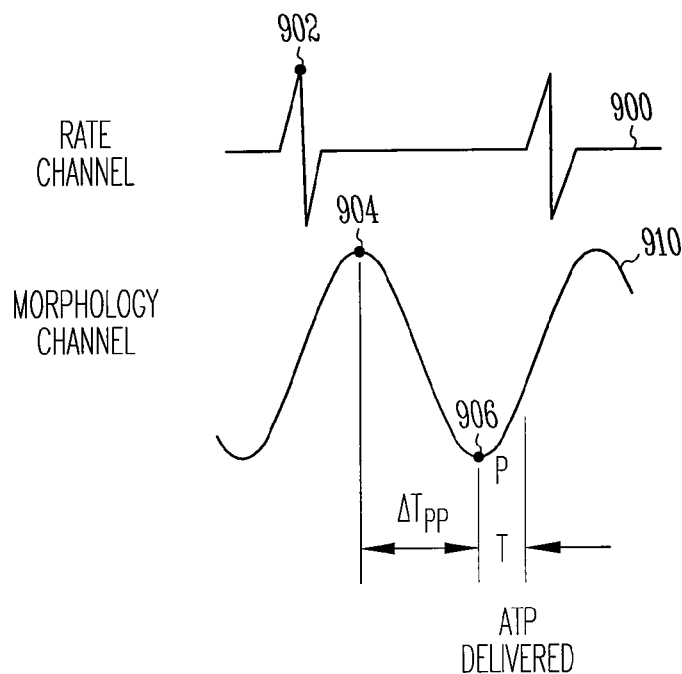
FIG. 9 is an illustration showing sensed cardiac signals and ATP timing determination.
Figure 10:
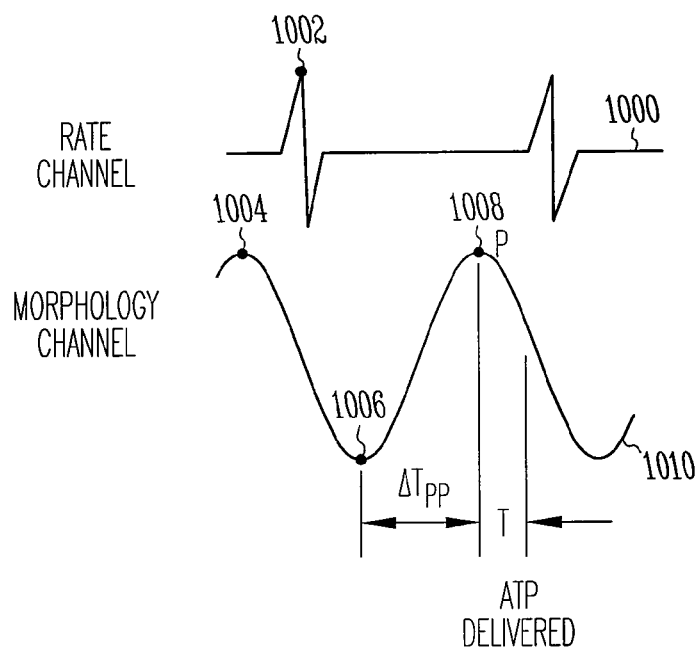
FIG. 10 is another illustration showing sensed cardiac signals and ATP timing determination.

FIGS. 9 and 10 illustrate cardiac signals sensed by sensing circuit 422 and ATP timing determination performed by morphology-based reference point detector 874 and morphology-based ATP interval generator 876. FIG. 9 illustrates a regional cardiac signal 900 sensed by rate channel 440, such as a regional ventricular electrogram, and a global cardiac signal 910 sensed by morphology channel 442, such as a global ventricular electrogram. A regional peak 902 (such as the R-wave peak in the regional ventricular electrogram) leads a corresponding global peak 904 (such as the corresponding R-wave peak in the global ventricular electrogram). The ATP reference point (P) is a global trough 906. The custom ATP interval (T) is the product of a constant (k) and the time interval between global peak 904 and global trough 906 ($\Delta T_{PP}$). That is: $T = k \cdot \Delta T_{PP}$. FIG. 10 illustrates a regional cardiac signal 1000 sensed by rate channel 440, such as a regional ventricular electrogram, and a global cardiac signal 1010 sensed by morphology channel 442, such as a global ventricular electrogram. A global peak 1004 (such as the R-wave peak in the global ventricular electrogram) leads a corresponding regional peak 1002 (such as the corresponding R-wave peak in the regional ventricular electrogram). The ATP reference point (P) is a global peak 1008. The custom ATP interval (T) is the product of the constant (k) and the time interval between global trough 1006 and global peak 1008 ($\Delta T_{PP}$). That is: $T = k \cdot \Delta T_{PP}$. With respect to both FIGS. 9 and 10, if the ATP therapy with the custom ATP interval (T) repeatedly fails to terminate the detected tachyarrhythmia episode (e.g., three times in a row), the value of the constant (k) is adjusted.

Figure 11A:
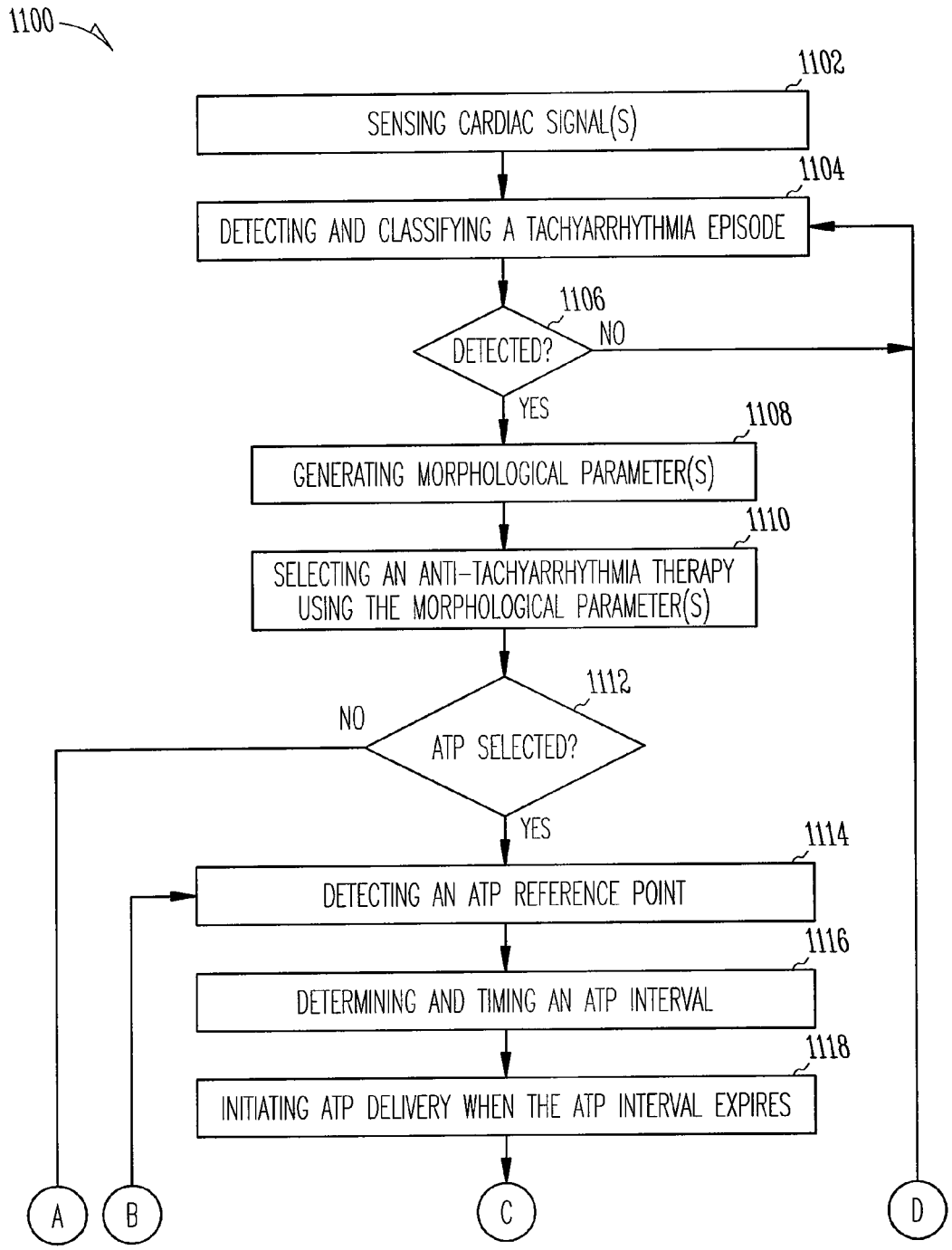
FIGS. 11A-B show a flow chart illustrating an embodiment of a method for selecting and timing anti-tachyarrhythmia therapies using cardiac signal morphology.
Figure 11B:
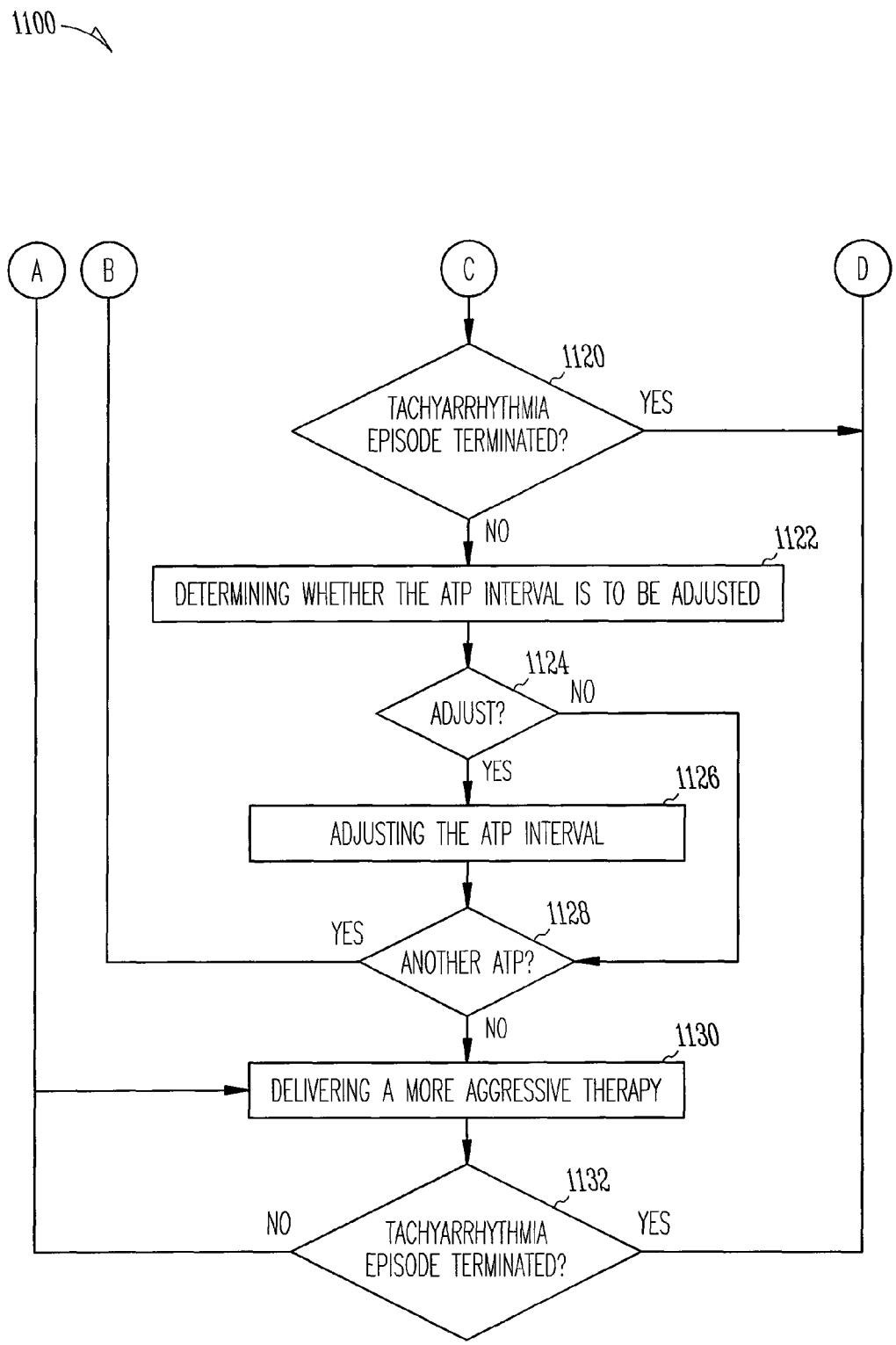

FIGS. 11A-B show a flow chart illustrating an embodiment of a method 1100 for selecting and timing anti-tachyarrhythmia therapies using cardiac signal morphology. In one embodiment, method 1100 is performed by system 100, including the various embodiments of its components discussed above and various combinations of these embodiments. In one embodiment, method 1100 is performed when ATP therapy is activated, such as by a prescription of a physician.

One or more cardiac signals are sensed at 1102. In one embodiment, a regional cardiac signal is sensed to provide for heart beat detection, and a global cardiac signal is sensed to provide for morphological analysis. In a specific embodiment, the regional cardiac signal is a regional ventricular electrogram sensed through two electrodes in the RV, and the global cardiac signal is a global ventricular electrogram sensed through an electrode in the RV and another electrode remote from the RV.

A tachyarrhythmia episode is detected and classified using the one or more sensed cardiac signals at 1104. In one embodiment, heart beats are detected from the regional cardiac signal. Cardiac cycle lengths, each being the time interval between two consecutively detected heart beats, are detected. The tachyarrhythmia episode is detected using the cardiac cycle lengths. When the cardiac cycle lengths falls into a tachyarrhythmia detection zone defined by one or more tachyarrhythmia detection thresholds for a predetermined number or percentage of consecutively detected heart beats, a detection of the tachyarrhythmia episode is declared. The detected tachyarrhythmia episode is classified using the global cardiac signal. In one embodiment, the detected tachyarrhythmia episode is classified as one of VT and SVT. In a specific embodiment, ventricular depolarizations (R waves) are detected as the hear beats from the regional ventricular electrogram. Ventricular cycle lengths (also referred to as ventricular intervals or R-R intervals) each being a time interval between two consecutively detected ventricular depolarizations are detected as the cardiac cycle lengths. The detection of a VT episode is declared when the ventricular cycle length falls within a VT detection zone for a predetermined number or percentage of consecutively detected ventricular depolarizations. The detection of the VT episode is confirmed by analyzing the morphology of the global ventricular electrogram. In one embodiment, a detection duration is initiated when the tachyarrhythmia episode is detected. The detected tachyarrhythmia episode is classified when the detection duration expires.

If an ATP-treatable tachyarrhythmia episode is detected (i.e., a tachyarrhythmia episode is detected and classified as a type treatable by an ATP therapy) at 1106, one or more morphological parameters are generated at 1108 for determining whether to deliver the ATP therapy and which ATP mode to select. In one embodiment, an ATP index for a heart beat is calculated using the one or more sensed cardiac signals. In a specific embodiment, a QT interval of the heart beat is detected, and the ATP index is calculated as the ratio of the QT interval to the cardiac cycle length associated with the heart beat. In another specific embodiment, a QRS width of the heart beat is detected, and the ATP index is calculated as the ratio of the QRS width to the cardiac cycle length associated with the heart beat. After ATP indexes are calculated for a plurality of heart beats, a mean ATP index of the ATP indexes and a standard deviation of the ATP indexes are calculated. In one embodiment, the mean ATP index of the ATP indexes is calculated for heart beats detected during the detection duration, and the standard deviation of the ATP indexes is calculated for the same heart beats detected during the detection duration.

An anti-tachyarrhythmia therapy is selected using the one or more morphological parameters at 1110. In one embodiment, an anti-tachyarrhythmia therapy is selected using the mean ATP index and the standard deviation. The ATP therapy with a default ATP mode is selected when the standard deviation is below a threshold standard deviation and the mean index is below a threshold index. The ATP therapy is diverted, and a more aggressive therapy mode is selected, when the standard deviation is below the threshold standard deviation and the mean index is above the threshold index and when the standard deviation is above the threshold standard deviation and at least a predetermined number of ATP indexes are above the threshold index. Examples of the more aggressive therapy include a cardioversion/defibrillation therapy and an ATP-BC therapy. The ATP therapy with a custom ATP mode is selected when the standard deviation is above the threshold standard deviation and at least a predetermined number of ATP indexes are below the threshold index. In one embodiment, the ATP therapy with a custom ATP mode is selected when the standard deviation is above the threshold standard deviation and the ATP indexes are below the threshold index for the last heart beats detected during the detection duration. The ATP therapy with the custom ATP mode uses at least one ATP parameter being a function of the morphology of the one or more cardiac signals.

If the ATP therapy is selected at 1112, an ATP reference point is detected at 1114, and an ATP interval is determined and timed at 1116. The ATP interval starts with the ATP reference point. The ATP therapy is initiated at the end of the ATP interval. When the ATP therapy with the default mode is selected, the ATP reference point is a cardiac depolarization detected from the regional cardiac signal, and a default ATP interval is produced. In one embodiment, the ATP reference point is a ventricular depolarization (R wave) detected from the regional ventricular electrogram, and the default ATP interval is calculated as a specified percentage of the average of ventricular cycle lengths detected for a plurality of consecutively detected heart beats preceding the ATP reference point. This default ATP interval is also known as the coupling interval. When the ATP therapy with the custom mode is selected, the ATP reference point and a custom ATP interval are determined using the morphology of the one or more cardiac signals. The ATP reference point is a predetermined type fiducial point on the global cardiac signal. In one embodiment, a regional peak in the regional cardiac signal, a global peak in the global cardiac signal, and a global trough adjacently following the global peak in the global cardiac signal are detected during a cardiac cycle. The ATP reference point is detected as the global trough if the global peak is between the regional peak and the global trough, or is the global peak if the global trough is between the regional peak and the global peak. The custom ATP interval is a product of a constant and a time interval between the global peak and the global trough.

The selected ATP therapy is delivered when the ATP interval expires at 1118. The ATP therapy includes at least one burst of pacing pulses.

If the detected tachyarrhythmia is not terminated by the ATP therapy at 1120, whether the ATP interval needs to be adjusted is determined at 1122. In one embodiment, the ATP interval determined at 1116 is evaluated using stored historical information including ATP intervals used in the past and their corresponding results in terminating tachyarrhythmia episodes. If the ATP interval is determined to be adjusted at 1124, for example, after the ATP interval determined at 1116 has failed to terminate several (e.g., three) tachyarrhythmia episodes in a row, the default ATP interval, the custom ATP interval, or the constant used in calculating the custom ATP interval is adjusted at 1126. If another attempt to terminate the detected tachyarrhythmia episode is set to be made at 1128, steps 1114 through 1128 are to be repeated. If no further attempt to terminate the detected tachyarrhythmia episode is set to be made at 1128, or if the ATP therapy is diverted at 1112, a more aggressive therapy such as the cardioversion/defibrillation therapy or the ATP-BC therapy is delivered at 1130. If the detected tachyarrhythmia is not terminated by the more aggressive therapy at 1132, steps 1130 and 1132 are repeated until the detected tachyarrhythmia is terminated.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management (CRM) system, comprising:
    a sensing circuit to sense one or more cardiac signals;
    a cycle length detector, coupled to the sensing circuit, to detect cardiac cycle lengths from the one or more cardiac signals, the cardiac cycle lengths each being a time interval between two consecutively detected heart beats;
    a tachyarrhythmia detector, coupled to the cycle length detector, to detect a tachyarrhythmia episode using the cardiac cycle lengths;
    a tachyarrhythmia classifier, coupled to the tachyarrhythmia detector, to classify the detected tachyarrhythmia episode;
    a pacing output circuit to deliver pacing pulses; and
    an anti-tachyarrhythmia pacing (ATP) selection module, coupled to the sensing circuit and the tachyarrhythmia classifier, to select a therapy mode based on the classification of the detected tachyarrhythmia episode and morphology of one of the one or more cardiac signals, the ATP selection module including:
        a morphological parameter generator including an ATP index calculator including a QRS width detector configured to detect QRS widths from the one of the one or more cardiac signals and a ratio calculator configured to calculate an ATP index as a ratio of the QRS width of a heart beat to the cardiac cycle length associated with the heart beat;
        a mean index calculator configured to calculate a mean ATP index of the ATP indexes calculated for a plurality of heart beats; and
        a standard deviation calculator configured to calculate a standard deviation of the ATP indexes calculated for the plurality of heart beats; and
    an ATP selector configured to select an ATP therapy from a plurality of therapies in response to the mean ATP index and the standard deviation indicating a likeliness of success of the ATP therapy.

2. The system of claim 1, wherein the tachyarrhythmia detection and classification module comprises a duration timer to initiate a detection duration in response to a detection of the tachyarrhythmia episode, and wherein the mean index calculator is configured to calculate the mean ATP index of the ATP indexes calculated for heart beats detected during the detection duration, and the standard deviation calculator is configured to calculate a standard deviation of the ATP indexes calculated for the heart beats detected during the detection duration.

3. The system of claim 1, wherein the ATP selector is configured to select the ATP therapy with a default ATP mode in response to the standard deviation being below a threshold standard deviation and the mean index being below a threshold index.

4. The system of claim 3, wherein the ATP selector is configured to divert from the ATP therapy in response to the standard deviation being below the threshold standard deviation and the mean index being above the threshold index and in response to the standard deviation being above the threshold standard deviation and at least a predetermined number of ATP indexes being above the threshold index.

5. The system of claim 4, wherein the ATP selector is configured to select the ATP therapy with a custom ATP mode using at least one ATP parameter being a function of the morphology of the one of the one or more cardiac signals in response to the standard deviation being above the threshold standard deviation and at least a predetermined number of ATP indexes being below the threshold index.

6. The system of claim 1, further comprising an ATP timing module coupled to sensing circuit, the ATP timing module configured to produce and time an ATP interval using the morphology of the one of the one or more cardiac signals and to initiate delivery of an ATP therapy upon expiration of the ATP interval.

7. The system of claim 6, wherein the ATP timing module comprises:
an ATP timer configured to start timing the ATP interval from an ATP reference point;
a morphology-based reference point detector configured to detect the ATP reference point being a predetermined type fiducial point on the one of one or more cardiac signals; and
a morphology-based ATP interval generator configured to produce the ATP interval using the morphology of the one of the one or more cardiac signals.

8. The system of claim 7, wherein the sensing circuit comprises:
a rate channel to sense a regional cardiac signal for detecting the tachyarrhythmia episode based on heart rate; and
a morphology channel to sense a global cardiac signal for morphological analysis.

9. The system of claim 8, wherein the morphology-based reference point detector is configured to detect:
a regional peak in the regional cardiac signal during a cardiac cycle;
a global peak in the global cardiac signal during the cardiac cycle;
a global trough adjacently following the global peak during the cardiac cycle;
the ATP reference point being the global trough if the global peak is between the regional peak and the global trough; and
the ATP reference point being the global peak if the global trough is between the regional peak leads the global peak.

10. The system of claim 9, wherein the morphology-based ATP interval generator is configured to calculate a custom ATP interval as a product of a constant and a time interval between the global peak and the global trough.

11. A cardiac rhythm management (CRM) system, comprising:
a sensing circuit to sense one or more cardiac signals;
a cycle length detector, coupled to the sensing circuit, to detect cardiac cycle lengths from the one or more cardiac signals, the cardiac cycle lengths each being a time interval between two consecutively detected heart beats;
a tachyarrhythmia detector, coupled to the cycle length detector, to detect a tachyarrhythmia episode using the cardiac cycle lengths;
a tachyarrhythmia classifier, coupled to the tachyarrhythmia detector, to classify the detected tachyarrhythmia episode;
a pacing output circuit to deliver pacing pulses;
an anti-tachyarrhythmia pacing (ATP) selection module, coupled to the sensing circuit and the tachyarrhythmia classifier, to select a therapy mode based on the classification of the detected tachyarrhythmia episode and morphology of one of the one or more cardiac signals, the ATP selection module including:
a morphological parameter generator including an ATP index calculator including a QRS width detector configured to detect QRS widths from the one of the one or more cardiac signals and a ratio calculator configured to calculate an ATP index as a ratio of the QRS width of a heart beat to the cardiac cycle length associated with the heart beat;
a mean index calculator configured to calculate a mean ATP index of the ATP indexes calculated for a plurality of heart beats; and
a standard deviation calculator configured to calculate a standard deviation of the ATP indexes calculated for the plurality of heart beats; and
an ATP selector configured to select an ATP therapy from a plurality of therapies in response to the mean ATP index and the standard deviation indicating a likeliness of success of the ATP therapy; and
an ATP timing module, coupled to the sensing circuit, the tachyarrhythmia classifier, and the pacing output circuit, the ATP timing module configured to time the delivery of the pacing pulses according to an ATP mode using the morphology of one cardiac signal of the one or more cardiac signals.

12. The system of claim 11, wherein the ATP selector is configured to select the ATP therapy with a default ATP mode in response to the standard deviation being below a threshold standard deviation and the mean ATP index being below a threshold index.

13. The system of claim 12, wherein the ATP selector is configured to divert from the ATP therapy in response to the standard deviation being below the threshold standard deviation and the mean ATP index being above the threshold index and in response to the standard deviation being above the threshold standard deviation and at least a predetermined number of ATP indexes being above the threshold index.

14. The system of claim 12, wherein the ATP selector is configured to select the ATP therapy with a custom ATP mode using at least one ATP parameter being a function of the morphology of the one of the one or more cardiac signals in response to the standard deviation being above the threshold standard deviation and at least a predetermined number of ATP indexes being below the threshold index.

15. The system of claim 14, wherein the ATP timing module is configured to produce and time an ATP interval and initiate the delivery of the pacing pulses according to the ATP mode in response to expiration of the ATP interval, the ATP timing module including:
an ATP timer configured to start timing the ATP interval from an ATP reference point;
a morphology-based reference point detector configured to detect the ATP reference point being a predetermined type fiducial point on one of the one or more cardiac signals; and
a morphology-based ATP interval generator configured to produce a custom ATP interval being the ATP interval for use with the custom ATP mode.

16. A cardiac rhythm management (CRM) system, comprising:
a sensing circuit to sense one or more cardiac signals;
a cycle length detector, coupled to the sensing circuit, to detect cardiac cycle lengths from the one or more cardiac signals, the cardiac cycle lengths each being a time interval between two consecutively detected heart beats;
a tachyarrhythmia detector, coupled to the cycle length detector, to detect a tachyarrhythmia episode using the cardiac cycle lengths;
a tachyarrhythmia classifier, coupled to the tachyarrhythmia detector, to classify the detected tachyarrhythmia episode;
a pacing output circuit to deliver pacing pulses;

an anti-tachyarrhythmia pacing (ATP) selection module, coupled to the sensing circuit and the tachyarrhythmia classifier, to select a therapy mode based on the classification of the detected tachyarrhythmia episode and morphology of one of the one or more cardiac signals, the ATP selection module including:
  a morphological parameter generator including an ATP index calculator including a QRS width detector configured to detect QRS widths from the one of the one or more cardiac signals and a ratio calculator configured to calculate an ATP index as a ratio of the QRS width of a heart beat to the cardiac cycle length associated with the heart beat;
    a mean index calculator configured to calculate a mean ATP index of the ATP indexes calculated for a plurality of heart beats; and
    a standard deviation calculator configured to calculate a standard deviation of the ATP indexes calculated for the plurality of heart beats; and
  an ATP selector configured to select an ATP therapy from a plurality of therapies in response to the mean ATP index and the standard deviation indicating a likeliness of success of the ATP therapy; and
an ATP timing module, coupled to the sensing circuit, the tachyarrhythmia classifier, and the pacing output circuit, to time the delivery of the pacing pulses according to an ATP mode using morphology of one cardiac signal of the one or more cardiac signals, the ATP timing module including:
  an ATP timer configured to start timing an ATP interval from an ATP reference point;
  a morphology-based reference point detector configured to detect the ATP reference point being a predetermined type fiducial point on the one cardiac signal of the one or more cardiac signals; and
  a morphology-based ATP interval generator configured to produce the ATP interval using the morphology of the one cardiac signal of the one or more cardiac signals.

17. The system of claim 16, wherein the ATP selector is configured to select the ATP therapy with a default ATP mode in response to the standard deviation being below a threshold standard deviation and the mean ATP index being below a threshold index.

18. The system of claim 17, wherein the ATP selector is configured to divert from the ATP therapy in response to the standard deviation being below the threshold standard deviation and the mean ATP index being above the threshold index and in response to the standard deviation being above the threshold standard deviation and at least a predetermined number of ATP indexes being above the threshold index.

19. The system of claim 18, wherein the ATP selector is configured to select the ATP therapy with a custom ATP mode using at least one ATP parameter being a function of the morphology of the one of the one or more cardiac signals in response to the standard deviation being above the threshold standard deviation and at least a predetermined number of ATP indexes being below the threshold index.

* * * * *